US009164093B2

(12) United States Patent
Yamashita et al.

(10) Patent No.: US 9,164,093 B2
(45) Date of Patent: Oct. 20, 2015

(54) CARDIOMYOCYTE MARKER (75) Inventors: Jun Yamashita, Kyoto (JP); Hideki Uosaki, Kyoto (JP)

(73) Assignee: IHEART JAPAN CORPORATION, Kyoto (JP)

( * ) Notice: Subject to any disclaimer, the term of this patent is extended or adjusted under 35 U.S.C. 154(b) by 0 days.

(21) Appl. No.: 14/009,064

(22) PCT Filed: Apr. 2, 2012

(86) PCT No.: PCT/JP2012/059617
§ 371 (c)(1),
(2), (4) Date: Oct. 28, 2013

(87) PCT Pub. No.: WO2012/133954
PCT Pub. Date: Oct. 4, 2012

(65) Prior Publication Data
US 2014/0057287 A1 Feb. 27, 2014

Related U.S. Application Data (60) Provisional application No. 61/470,101, filed on Mar. 31, 2011.

(51) Int. Cl.
*G01N 33/569* (2006.01)
*C12N 5/077* (2010.01)
(52) U.S. Cl.
CPC ........ *G01N 33/56966* (2013.01); *C12N 5/0657* (2013.01); *C12N 2501/115* (2013.01); *C12N 2501/155* (2013.01); *C12N 2501/16* (2013.01); *C12N 2506/02* (2013.01); *C12N 2506/45* (2013.01)

(58) Field of Classification Search
CPC .......... G01N 33/56966; C12N 5/0657; C12N 2501/155; C12N 2501/16; C12N 2506/02; C12N 2506/45
See application file for complete search history.

(56) References Cited

U.S. PATENT DOCUMENTS

| | | | |
|---|---|---|---|
| 2007/0010012 A1 | 1/2007 | Gold et al. | |
| 2009/0068742 A1 | 3/2009 | Yamanaka et al. | |
| 2011/0104122 A1 | 5/2011 | Yamashita et al. | |
| 2014/0329314 A1* | 11/2014 | O'Sullivan et al. | 435/366 |

FOREIGN PATENT DOCUMENTS

| | | |
|---|---|---|
| JP | 2010-158206 | 7/2010 |
| WO | WO 2007/002136 A1 | 1/2007 |

(Continued)

OTHER PUBLICATIONS

Matsuura et al. Adult Cardiac Progenitor Cells Promote Angiogenesis and Cardioprotection through their Secreted Soluble Vcam-1, Circulation 118 (18): Suppl. 2, pp. S396 (Oct. 28, 2008).*

(Continued)

*Primary Examiner* — Gail R Gabel
(74) *Attorney, Agent, or Firm* — Knobbe, Martens, Olson & Bear, LLP (57) ABSTRACT The present invention provides a method for production or detection of a cardiomyocyte(s) and/or cardiac progenitor cell(s), comprises extracting a cardiomyocyte(s) and/or cardiac progenitor cell(s) from a cell population comprising cardiomyocytes and/or cardiac progenitor cells using as an index VCAM1 positivity.

12 Claims, 4 Drawing Sheets

(56) References Cited

FOREIGN PATENT DOCUMENTS

| WO | WO 2007/069666 A2 | 6/2007 |
| WO | WO 2009/118928 A1 | 10/2009 |
| WO | WO 2012/135253 A1 | 10/2012 |

OTHER PUBLICATIONS

Uosaki et al. Efficient and Scalable Purification of Cardiomyocytes from Human Embryonic and Induced Pluripotent Stem Cells by VCAM1 Surface Expression, PloS One 6 (8): e23657 pp. 1-9 (Aug. 2011).*

Honda, et al., "N-cadherin is a useful marker for the progenitor of cardiomyocytes differentiated from mouse ES cells in serum-free condition," *Biochemical and Biophysical Research Communications*, vol. 351, pp. 877-882 (Oct. 2006).

Kattman, et al., "Stage-Specific Optimization of Activin/Nodal and BMP Signaling Promotes Cardiac Differentiation of Mouse and Human Pluripotent Stem Cell Lines," *Cell Stem Cell*, vol. 8(2), pp. 228-240 (Feb. 4, 2011).

Rust, et al., "Cardiomyocyte enrichment from human embryonic stem cell cultures by selection of ALCAM surface expression," *Regen. Med.*, vol. 4(2), pp. 225-237 (2009).

Uosaki, et al., "Efficient and Scalable Purification of Cariomyocytes from Human Embryonic and Induced Pluripotent Stem Cells by VCAM1 Surface Expression," *PLoS One*, vol. 6(8) pp. 1-9 (Aug. 2011).

Xu, "Differentiation and enrichment of cardiomyocytes from human pluripotent stem cells," *Journal of Molecular and Cellular Cardiology*, vol. 52(6), pp. 1203-1212 (2012).

Yan, et al., "Cyclosporin-A potently induces highly cardiogenic progenitors from embryonic stem cells," *Biochemical and Biophysical Research Communications*, vol. 379, pp. 115-120 (2009).

Elliott et al., Nature Methods, vol. 8, No. 12, Dec. 2011, pp. 1037-1040 with Online Methods.

Hattori et al., Biochemistry and Molecular Biology International, vol. 41, No. 5, Apr. 1997, pp. 979-986.

Matsuura et al., Journal of Clinical Investigation, vol. 119, No. 8, 2009, pp. 2204-2217.

Molossi et al., Journal of Pathology, vol. 176, No. 2, 1995, pp. 175-182.

Skelton et al., Stem Cell Research, vol. 13, No. 1, 2014, pp. 172-179.

Extended European Search Report from European counterpart application 12765553.8, dated Aug. 1, 2014.

Uosaki, et al., "Efficient and Scalable Purification of Cariomyocytes from Human Embryonic and Induced Pluripotent Stem Cells by VCAM1 Surface Expression," *PLoS One*, vol. 6(8), e23657 (Aug. 2011).

* cited by examiner

CARDIOMYOCYTE MARKER

TECHNICAL FIELD

The present invention relates to a novel cardiomyocyte marker; and a method for producing cardiomyocytes and/or cardiac progenitor cells, a method for detecting cardiomyocytes and/or cardiac progenitor cells and a kit for extracting or detecting cardiomyocytes and/or cardiac progenitor cells, using the marker.

BACKGROUND ART

Cardiomyocytes lose their division potential at the time of birth and hence their regeneration is difficult. Therefore, recent interest has focused on replacement therapy wherein cardiomyocytes obtained by differentiation induction of cells having pluripotency (WO/2007/069666), such as embryonic stem cells (ES cells) and induced pluripotent stem cells (iPS cells), are transplanted to a cardiac tissue that has been damaged due to myocardial infarction, myocarditis, aging or the like. Although many methods for differentiation induction of such pluripotent stem cells into cardiomyocytes have been reported (WO2007/002136, WO2009/118928 and Yan P, et al., Biochem Biophys Res Commun. 379:115-20 (2009)), it is necessary to enhance the purity of the cardiomyocytes by sorting or the like for using the induced cells in transplantation. Although, at present, CD166 (ALCM) (Rust W, et al., Regen Med. 4, 225-37 (2009)), N-cadherin (JP 2010-158206 A and Honda M, et al., Biochem Biophys Res Commun. 29, 351, 877-82 (2006)) and the like have been reported as surface markers for cardiomyocytes and/or cardiac progenitor cells, it is necessary to find more markers for enhancing the purity of cardiomyocytes.

SUMMARY OF THE INVENTION

An object of the present invention is to extract cardiomyocytes and/or cardiac progenitor cells from a cell population comprising the cardiomyocytes and/or cardiac progenitor cells. Therefore, the present invention aims to provide a marker specific to cardiomyocytes and/or cardiac progenitor cells.

In order to solve the above object, the inventors of the present invention focused on a cell surface membrane protein VCAM1 and found that cardiomyocytes and/or cardiac progenitor cells can be obtained from a cell population containing the cardiomyocytes and/or cardiac progenitor cells by using as an index the VCAM1 positivity. It was also found that, by further using as an index the PDGFRβ positivity or N-cadherin positivity, cardiomyocytes and/or cardiac progenitor cells can be obtained at a higher rate.

From the above results, the present inventors succeeded in isolation/purification of cardiomyocytes and/or cardiac progenitor cells, thereby completed the present invention.

An aspect of the present invention is to provide a method for producing a cardiomyocyte(s) and/or cardiac progenitor cell(s), comprising extracting a cardiomyocyte(s) and/or cardiac progenitor cell(s) from a cell population comprising cardiomyocytes and/or cardiac progenitor cells using as an index VCAM1 positivity.

Another aspect of the present invention is to provide the method as described above, further comprising extracting a cardiomyocyte(s) and/or cardiac progenitor cell(s) using as an index PDGFRβ negativity.

Another aspect of the present invention is to provide the method as described above, further comprising extracting a cardiomyocyte(s) and/or cardiac progenitor cell(s) using as an index N-cadherin positivity.

Another aspect of the present invention is to provide the method as described above, wherein the cardiomyocyte(s) and/or cardiac progenitor cell(s) is/are a human cardiomyocyte(s) and/or human cardiac progenitor cell(s).

Another aspect of the present invention is to provide the method as described above, wherein the cell population is a cell population comprising cardiomyocytes and/or cardiac progenitor cells the differentiation of which has been induced from pluripotent stem cells, or a cell population composed of cells from an isolated tissue.

Another aspect of the present invention is to provide the method as described above, wherein the differentiation induction into cardiomyocytes and/or cardiac progenitor cells is differentiation induction by culturing in a medium containing a cytokine(s).

Another aspect of the present invention is to provide the method as described above, wherein the cytokine(s) is/are at least one cytokine selected from the group consisting of activin A and BMP4 (bone morphogenetic protein 4).

Another aspect of the present invention is to provide a method for detecting a cardiomyocyte(s) and/or cardiac progenitor cell(s), comprising detecting a cardiomyocyte(s) and/or cardiac progenitor cell(s) from a cell population comprising cardiomyocytes and/or cardiac progenitor cells using as an index VCAM1 positivity.

Another aspect of the present invention is to provide the detection method as described above, further comprising detecting a cardiomyocyte(s) and/or cardiac progenitor cell(s) using as an index PDGFRβ negativity.

Another aspect of the present invention is to provide the detection method as described above, further comprising detecting a cardiomyocyte(s) and/or cardiac progenitor cell(s) using as an index N-cadherin positivity.

Another aspect of the present invention is to provide the detection method as described above, wherein the cardiomyocyte(s) and/or cardiac progenitor cell(s) is/are a human cardiomyocyte(s) and/or human cardiac progenitor cell(s)

Another aspect of the present invention is to provide the detection method as described above, wherein the cell population is a cell population comprising cardiomyocytes and/or cardiac progenitor cells the differentiation of which has been induced from pluripotent stem cells, or a cell population composed of cells from an isolated tissue.

Another aspect of the present invention is to provide a kit for extraction or detection of a cardiomyocyte(s) and/or cardiac progenitor cell(s), comprising a reagent having affinity to VCAM1.

Another aspect of the present invention is to provide the kit as described above, further comprising a reagent having affinity to PDGFRβ.

Another aspect of the present invention is to provide the kit as described above, further comprising a reagent having affinity to N-cadherin.

Another aspect of the present invention is to provide the kit as described above, wherein the cardiomyocyte(s) and/or cardiac progenitor cell(s) is/are a human cardiomyocyte(s) and/or human cardiac progenitor cell(s).

DESCRIPTION OF THE PREFERRED EMBODIMENTS

The present invention will now be described below in detail.

As described above, the present invention relates to a method for producing a cardiomyocyte(s) and/or cardiac progenitor cell(s), comprising extracting a cardiomyocyte(s) and/or cardiac progenitor cell(s) from a cell population comprising cardiomyocytes and/or cardiac progenitor cells using as an index the VCAM1 positivity; and a method for detecting a cardiomyocyte(s) and/or cardiac progenitor cell(s), comprising detecting a cardiomyocyte(s) and/or cardiac progenitor cell(s) from a cell population comprising cardiomyocytes and/or cardiac progenitor cells using as an index the VCAM positivity.

In the present invention, the origin of the cell population comprising cardiomyocytes and/or cardiac progenitor cells is not restricted as long as the cell population comprises cardiomyocytes and/or cardiac progenitor cells. Examples of the cell population comprising cardiomyocytes and/or cardiac progenitor cells include cells contained in peripheral blood, heart, myeloid tissue, adipose tissue, skeletal muscle tissue, amniotic tissue, placental tissue, umbilical cord blood or the like obtained by an arbitrary method, and cells comprising cardiomyocytes and/or cardiac progenitor cells the differentiation of which has been induced from pluripotent stem cells.

In the present invention, the extraction of cardiomyocytes and/or cardiac progenitor cells means to increase the ratio of cardiomyocytes and/or cardiac progenitor cells relative to other types of cells, and the cardiomyocytes and/or cardiac progenitor cells are preferably concentrated such that they are contained at a ratio of not less than 50%, 60%, 70%, 80% or 90% in the cell population. More preferably, the extraction of cardiomyocytes and/or cardiac progenitor cells means to purify cardiomyocytes and/or cardiac progenitor cells to a ratio of 100% in the cell population.

In the present invention, VCAM1 is a protein known as vascular cell adhesion molecule 1 (VCAM-1) or CD106, which is involved in cell adhesion. For example, in the case of human, VCAM1 is encoded by the gene described in NCBI (National Center for Biotechnology Information) accession No. NM_001078, NM_001199834 or NM_080682, and has 6 or 7 immunoglobulin domains. VCAM1 also includes isoforms produced by alternative splicing.

In the present invention, a step of extracting or detecting PDGFRβ-negative cells as cardiomyocytes and/or cardiac progenitor cells may be further performed. PDGFRβ herein means the cell surface receptor known as platelet-derived growth factor receptor, beta polypeptide or PDGFR1. For example, in the case of human, the gene encoding PDGFRβ comprises the nucleotide sequence described in NCBI accession No. NM_002609.

In the present invention, a step of extracting or detecting N-cadherin-positive cells as cardiomyocytes and/or cardiac progenitor cells may be further performed. N-cadherin herein means the gene known as CDH2, which is involved in cell adhesion. For example, in the case of human, the gene encoding N-cadherin is described in NCBI accession No. NM_001792 or the protein encoded by this sequence, and extracellularly has 5 repeats each having about 100 amino acids (EC domain).

In the present invention, "cardiomyocytes" means cells of cardiac muscle having the property of self-beating. "Cardiac progenitor cells" means progenitor cells of such cardiomyocytes, which progenitor cells have an ability to produce cardiomyocytes that form beating muscle and electrically conductive tissues, and vascular smooth muscle. Here, the cardiomyocytes and the cardiac progenitor cells may be either coexisting with or isolated from each other.

The cardiomyocytes and the cardiac progenitor cells are characterized in that these are positive for cardiac troponin (cTnT or troponin T type 2), which is a myocardial marker, and/or for αMHC (α myosin heavy chain).

<Pluripotent Stem Cells>

The pluripotent stem cells, which may be used in the present invention, are stem cells having pluripotency which enables the cells to differentiate into any cells existing in the living body, and also having growth ability. Examples of the pluripotent stem cells include, but are not limited to, embryonic stem (ES) cells, embryonic stem cells derived from a cloned embryo obtained by nuclear transfer (ntES cells), germline stem cells ("GS cells"), embryonic germ cells ("EG cells") and induced pluripotent stem (iPS) cells. Preferred examples of the pluripotent stem cells include ES cells, ntES cells and iPS cells.

(A) Embryonic Stem Cells

ES cells are stem cells established from the inner cell mass of an early embryo (for example, blastocyst) of a mammal such as human or mouse, and have pluripotency and growth ability by self-renewal.

ES cells are embryo-derived stem cells originated from the inner cell mass of a blastocyst which is the embryo formed following the 8-cell stage and the morula stage of a fertilized egg, and ES cells have ability to differentiate into any cells constituting an adult, that is, the so called pluripotency of differentiation, and growth ability by self-renewal. ES cells were discovered in mouse in 1981 (M. J. Evans and M. H. Kaufman (1981), Nature 292:154-156), and followed by establishment of ES cell lines of primates such as human and monkey (J. A. Thomson et al. (1998), Science 282:1145-1147; J. A. Thomson et al. (1995), Proc. Natl. Acad. Sci. USA, 92:7844-7848; J. A. Thomson et al. (1996), Biol. Reprod., 55:254-259; J. A. Thomson and V. S. Marshall (1998), Curr. Top. Dev. Biol., 38:133-165).

ES cells can be established by removing the inner cell mass from the blastocyst of a fertilized egg of the subject animal, followed by culturing the inner cell mass on fibroblasts as feeders. The cells can be maintained by subculturing using a medium supplemented with substances such as leukemia inhibitory factor (LIF) and/or basic fibroblast growth factor (bFGF). Methods of establishment and maintenance of human and monkey ES cells are described in, for example, U.S. Pat. No. 5,843,780 B; Thomson J A, et al. (1995), Proc Natl. Acad. Sci. USA. 92:7844-7848; Thomson J A, et al. (1998), Science. 282:1145-1147; H. Suemori et al. (2006), Biochem. Biophys. Res. Commun., 345:926-932; M. Ueno et al. (2006), Proc. Natl. Acad. Sci. USA, 103:9554-9559; H. Suemori et al. (2001), Dev. Dyn., 222:273-279; H. Kawasaki et al. (2002), Proc. Natl. Acad. Sci. USA, 99:1580-1585; and Klimanskaya I, et al. (2006), Nature. 444:481-485.

In terms of the medium for preparation of ES cells, human ES cells can be maintained, for example, using DMEM/F-12 medium supplemented with 0.1 mM 2-mercaptoethanol, 0.1 mM non-essential amino acids, 2 mM L-glutamic acid, 20% KSR and 4 ng/ml bFGF at 37° C. under a moist atmosphere of 2% $CO_2$/98% air (O. Fumitaka et al. (2008), Nat. Biotechnol., 26:215-224). Further, ES cells need to be subcultured every 3 to 4 days, and the subculture can be carried out using 0.25% trypsin and 0.1 mg/ml collagenase IV in PBS supplemented with 1 mM $CaCl_2$ and 20% KSR.

Selection of ES cells can be generally carried out by the Real-Time PCR method using as an index/indices expression of a gene marker(s) such as alkaline phosphatase, Oct-3/4 and/or Nanog. In particular, for selection of human ES cells, expression of a gene marker(s) such as OCT-3/4, NANOG and/or ECAD can be used as indices (E. Kroon et al. (2008), Nat. Biotechnol., 26:443-452).

For example, in terms of human ES cell lines, WA01(H1) and WA09(H9) can be obtained from WiCell Research Institute, and KhES-1, KhES-2 and KhES-3 can be obtained from Institute for Frontier Medical Sciences, Kyoto University (Kyoto, Japan).

(B) Germline Stem Cells

Germline stem cells are pluripotent stem cells derived from testis, and play a role as the origin for spermatogenesis. Similarly to ES cells, these cells can be induced to differentiate into various series of cells, and, for example, have a property to enable preparation of a chimeric mouse by transplantation of the cells to a mouse blastocyst (M. Kanatsu-Shinohara et al. (2003) Biol. Reprod., 69:612-616; K. Shinohara et al. (2004), Cell, 119:1001-1012). Germline stem cells are capable of self-renewal in a medium containing glial cell line-derived neurotrophic factor (GDNF), and, by repeating subculture under the same culture conditions as those for ES cells, germline stem cells can be obtained (Masanori Takehashi et al. (2008), Experimental Medicine, 26(5) (extra edition):41-46, Yodosha (Tokyo, Japan)).

(C) Embryonic Germ Cells

Embryonic germ cells are established from fetal primordial germ cells and have pluripotency similar to that of ES cells. They can be established by culturing primordial germ cells in the presence of substances such as LIF, bFGF and stem cell factor (Y. Matsui et al. (1992), Cell, 70:841-847; J. L. Resnick et al. (1992), Nature, 359:550-551).

(D) Induced Pluripotent Stem Cells

Induced pluripotent stem (iPS) cells can be prepared by introducing specific reprogramming factors to somatic cells, which reprogramming factors may be in the form of DNA or protein. iPS cells are somatic cell-derived artificial stem cells having properties almost equivalent to those of ES cells, such as pluripotency of differentiation and growth ability by self-renewal (K. Takahashi and S. Yamanaka (2006) Cell, 126: 663-676; K. Takahashi et al. (2007), Cell, 131:861-872; J. Yu et al. (2007), Science, 318:1917-1920; Nakagawa, M. et al., Nat. Biotechnol. 26:101-106 (2008); WO 2007/069666). The reprogramming factors may be constituted by genes or gene products thereof, or non-coding RNAs, which are expressed specifically in ES cells; or genes or gene products thereof, or non-coding RNAs, which play important roles in maintenance of the undifferentiated state of ES cells; or low molecular weight compounds. Examples of the genes included in the reprogramming factors include Oct3/4, Sox2, Sox1, Sox3, Sox15, Sox17, Klf4, Klf2, c-Myc, N-Myc, L-Myc, Nanog, Lin28, Fbx15, ERas, ECAT15-2, Tcl1, beta-catenin, Lin28b, Sall1, Sall4, Esrrb, Nr5a2, Tbx3 and Glis1 and these reprogramming factors may be used either alone or in combination. Examples of the combinations of the reprogramming factors include those described in WO2007/069666; WO2008/118820; WO2009/007852; WO2009/032194; WO2009/058413; WO2009/057831; WO2009/075119; WO2009/079007; WO2009/091659; WO2009/101084; WO2009/101407; WO2009/102983; WO2009/114949; WO2009/117439; WO2009/126250; WO2009/126251; WO2009/126655; WO2009/157593; WO2010/009015; WO2010/033906; WO2010/033920; WO2010/042800; WO2010/050626; WO 2010/056831; WO2010/068955; WO2010/098419; WO2010/102267; WO 2010/111409; WO 2010/111422; WO2010/115050; WO2010/124290; WO2010/147395; WO2010/147612; Huangfu D, et al. (2008), Nat. Biotechnol., 26: 795-797; Shi Y, et al. (2008), Cell Stem Cell, 2: 525-528; Eminli S, et al. (2008), Stem Cells. 26:2467-2474; Huangfu D, et al. (2008), Nat Biotechnol. 26:1269-1275; Shi Y, et al. (2008), Cell Stem Cell, 3, 568-574; Zhao Y, et al. (2008), Cell Stem Cell, 3:475-479; Marson A, (2008), Cell Stem Cell, 3, 132-135; Feng B, et al. (2009), Nat Cell Biol. 11:197-203; R. L. Judson et al., (2009), Nat. Biotech., 27:459-461; Lyssiotis C A, et al. (2009), Proc Natl Acad Sci USA. 106:8912-8917; Kim J B, et al. (2009), Nature. 461: 649-643; Ichida J K, et al. (2009), Cell Stem Cell. 5:491-503; Heng J C, et al. (2010), Cell Stem Cell. 6:167-74; Han J, et al. (2010), Nature. 463:1096-100; Mali P, et al. (2010), Stem Cells. 28:713-720; and Maekawa M, et al. (2011), Nature. 474:225-229.

Examples of reprogramming factors also include histone deacetylase (HDAC) inhibitors [for example, low molecular weight inhibitors such as valproic acid (VPA), trichostatin A, sodium butyrate, MC 1293 and M344; and nucleic acid-type expression inhibitors such as siRNAs and shRNAs against HDAC (e.g., HDAC1 siRNA Smartpool® (Millipore) and HuSH 29mer shRNA Constructs against HDAC1 (Ori-Gene))], MEK inhibitors (for example, PD184352, PD98059, U0126, SL327 and PD0325901), Glycogen synthase kinase-3 inhibitors (for example, Bio and CHIR99021), DNA methyltransferase inhibitors (for example, 5'-azacytidine), histone methyltransferase inhibitors (for example, low molecular weight inhibitors such as BIX-01294; and nucleic acid-type expression inhibitors such as siRNAs and shRNAs against Suv39h1, Suv39h2, SetDB1 and G9a), L-channel calcium agonists (for example, Bayk8644), butyric acid, TGFβ inhibitors or ALK5 inhibitors (for example, LY364947, SB431542, 616453 and A-83-01), p53 inhibitors (for example, siRNAs and shRNAs against p53), ARID3A inhibitors (for example, siRNAs and shRNAs against ARID3A), miRNAs such as miR-291-3p, miR-294, miR-295 and mir-302, Wnt Signaling (for example, soluble Wnt3a), neuropeptide Y, prostaglandins (for example, prostaglandin E2 and prostaglandin J2), hTERT, SV40LT, UTF1, IRX6, GLIS1, PITX2 and DMRTB1, which are employed for enhancing the establishment efficiency, and, in the present description, these factors employed for the purpose of enhancement of the establishment efficiency are not particularly distinguished from the above-described reprogramming factors.

In cases where the reprogramming factors are in the form of protein, the reprogramming factors may be introduced into somatic cells by a method such as lipofection, fusion with a cell-permeable peptide (e.g., HIV-derived TAT or polyarginine), or microinjection.

In cases where the reprogramming factors are in the form of DNA, the reprogramming factors may be introduced into somatic cells by a method such as use of a vector including virus, plasmid and artificial chromosome vectors; lipofection; use of liposome; or microinjection. Examples of the virus vector include retrovirus vectors, lentivirus vectors (these are described in Cell, 126, pp. 663-676, 2006; Cell, 131, pp. 861-872, 2007; and Science, 318, pp. 1917-1920, 2007), adenovirus vectors (Science, 322, 945-949, 2008), adeno-associated virus vectors and Sendai virus vectors (WO 2010/008054). Examples of the artificial chromosome vector include human artificial chromosome (HAC), yeast artificial chromosome (YAC), and bacterial artificial chromosome (BAC and PAC). Examples of the plasmid which may be used include plasmids for mammalian cells (Science, 322:949-953, 2008). The vectors may contain a regulatory sequence(s) such as a promoter, enhancer, ribosome binding sequence, terminator and/or polyadenylation site; and, as required, a sequence of a selection marker such as a drug resistance gene (e.g., kanamycin-resistant gene, ampicillin-resistant gene or puromycin-resistant gene), thymidine kinase gene or diphtheria toxin gene; a gene sequence of a reporter such as the green-fluorescent protein (GFP), β-glucuronidase (GUS) or FLAG; and/or the like to enable expression of the nuclear reprogramming factors. Further, in order to remove, after introduction of the above vector into somatic cells, the genes encoding the reprogramming factors, or both the promoters and the genes encoding the reprogramming factors linked thereto, the vector may have loxP sequences in the upstream and the downstream of these sequences.

Further, in cases where the reprogramming factors are in the form of RNA, each reprogramming factor may be introduced into somatic cells by a method such as lipofection or microinjection, and an RNA into which 5-methylcytidine and pseudouridine (TriLink Biotechnologies) were incorporated may be used in order to suppress degradation (Warren L, (2010) Cell Stem Cell. 7:618-630).

Examples of the medium for induction of the iPS cells include the DMEM, DMEM/F12 and DME media supplemented with 10 to 15% FBS (these media may further contain LIF, penicillin/streptomycin, puromycin, L-glutamine, non-essential amino acids, β-mercaptoethanol and/or the like, as appropriate); and commercially available media [for example, medium for culturing mouse ES cells (TX-WES medium, Thromb-X), medium for culturing primate ES cells (medium for primate ES/iPS cells, ReproCELL) and serum-free medium (mTeSR, Stemcell Technology)].

Examples of the culture method include a method wherein somatic cells and reprogramming factors are brought into contact with each other at 37° C. in the presence of 5% $CO_2$ on DMEM or DMEM/F12 medium supplemented with 10% FBS, and the cells are cultured for about 4 to 7 days, followed by plating the cells on feeder cells (e.g., mitomycin C-treated STO cells or SNL cells) and starting culture in a bFGF-containing medium for culturing primate ES cells about 10 days after the contact between the somatic cells and the reprogramming factors, thereby allowing iPS-like colonies to appear about 30 to about 45 days after the contact, or later.

Alternatively, the cells may be cultured at 37° C. in the presence of 5% $CO_2$ on feeder cells (e.g., mitomycin C-treated STO cells or SNL cells) in the DMEM medium supplemented with 10% FBS (this medium may further contain LIF, penicillin/streptomycin, puromycin, L-glutamine, non-essential amino acids, β-mercaptoethanol and/or the like, as appropriate) for about 25 to about 30 days or longer, thereby allowing ES-like colonies to appear. Preferred examples of the culture method include a method wherein the somatic cells themselves to be reprogrammed are used instead of the feeder cells (Takahashi K, et al. (2009), PLoS One. 4:e8067 or WO2010/137746), and a method wherein an extracellular matrix (e.g., Laminin-5 (WO2009/123349) or Matrigel (BD)) is used instead.

Other examples include a method wherein the culture is carried out using a serum-free medium (Sun N, et al. (2009), Proc Natl Acad Sci USA. 106:15720-15725). Further, in order to enhance the establishment efficiency, iPS cells may be established under low oxygen conditions (at an oxygen concentration of not less than 0.1% and not more than 15%) (Yoshida Y, et al. (2009), Cell Stem Cell. 5:237-241 or WO2010/013845).

During the culture, the medium is replaced with a fresh medium once every day from Day 2 of the culture. The number of the somatic cells used for nuclear reprogramming is not restricted, and usually within the range of about $5 \times 10^3$ to about $5 \times 10^6$ cells per 100-$cm^2$ area on the culture dish.

iPS cells may be selected based on the shape of each formed colony. In cases where a drug resistance gene, which is expressed in conjunction with a gene being expressed upon reprogramming of a somatic cell (e.g., Oct3/4 or Nanog), is introduced as a marker gene, established iPS cells can be selected by culturing the cells in a medium containing the corresponding drug (selection medium). Further, iPS cells can be selected by observation under a fluorescence microscope in cases where the marker gene is the gene of a fluorescent protein; by adding a luminescent substrate in cases where the marker gene is the gene of luciferase; or by adding a coloring substrate in cases where the marker gene is the gene of a coloring enzyme.

The term "somatic cells" used in the present description means any animal cells (preferably cells of mammals including human) excluding germ-line cells and totipotent cells such as eggs, oocytes and ES cells. Examples of the somatic cells include, but are not limited to, any of fetal somatic cells, neonatal somatic cells, and mature, healthy and diseased somatic cells, as well as any of primary cultured cells, subcultured cells and established cell lines. Particular examples of the somatic cells include (1) tissue stem cells (somatic stem cells) such as neural stem cells, hematopoietic stem cells, mesenchymal stem cells and dental pulp stem cells; (2) tissue progenitor cells; and (3) differentiated cells such as lymphocytes, epithelial cells, endothelial cells, muscle cells, fibroblasts (skin cells and the like), hair cells, hepatic cells, gastric mucosal cells, enterocytes, spleen cells, pancreatic cells (pancreatic exocrine cells and the like), brain cells, lung cells, kidney cells and adipocytes.

In cases where iPS cells are used as a material for cells to be transplanted, somatic cells whose HLA genotype is the same or substantially the same as that of the individual to which the cells are to be transplanted are preferably used in view of prevention of the rejection reaction. Here, "substantially the same" means that the HLA genotype is matching to an extent at which the immune reaction against the transplanted cells can be suppressed with an immunosuppressive agent. For example, the somatic cells have matched HLA types at 3 loci HLA-A, HLA-B and HLA-DR, or at 4 loci further including HLA-C.

(E) ES Cells Derived from Cloned Embryo Obtained by Nuclear Transfer ntES cells are ES cells derived from a cloned embryo prepared by the nuclear transfer technique, and have properties which are almost the same as those of ES cells derived from fertilized eggs (T. Wakayama et al. (2001), Science, 292:740-743; S. Wakayama et al. (2005), Biol. Reprod., 72:932-936; J. Byrne et al. (2007), Nature, 450:497-502). That is, an ntES (nuclear transfer ES) cell is an ES cell established from the inner cell mass of a blastocyst derived from a cloned embryo obtained by replacement of the nucleus of an unfertilized egg with the nucleus of a somatic cell. For preparation of an ntES cell, the combination of the nuclear transfer technique (J. B. Cibelli et al. (1998), Nature Biotechnol., 16:642-646) and the ES cell preparation technique (described above) is employed (Sayaka Wakayama et al. (2008), Experimental Medicine 26(5) (extra edition):47-52). In nuclear transfer, reprogramming can be achieved by injecting the nucleus of a somatic cell into a mammalian enucleated unfertilized egg and culturing the resultant for several hours.

<Method for Preparing Cardiomyocytes and/or Cardiac Progenitor Cells from Pluripotent Stem Cells>

The method of differentiation induction of pluripotent stem cells into cardiomyocytes and/or cardiac progenitor cells is not restricted, and, for example, the following method may be used.

Pluripotent stem cells may be separated by an arbitrary method and subjected to suspension culture, or adherent culture using a coated culture dish. In the method of separation, the cells may be mechanically separated, or may be separated using an EDTA solution (e.g., 0.5 mM EDTA solution or Versene (Invitrogen)), separation solution having protease activity and collagenase activity (e.g., Accutase™ or Accumax™), or separation solution having only collagenase activity. In the suspension culture, the culture dish to be used may have either a surface which is not artificially treated for the purpose of enhancing adhesiveness to cells (for example, by coating treatment with an extracellular matrix or the like) or a surface which is artificially treated such that adhesion is suppressed (for example, by coating treatment with polyhydroxyethylmethacrylate (poly-HEMA)). In the adherent culture, the culture dish to be used may be one coated with Matrigel (BD), type I collagen, type IV collagen, gelatin, laminin, heparan sulfate proteoglycan or entactin, or a combinations thereof.

The suspension culture and the adherent culture may be performed in combination. In an embodiment of the present invention where these are performed in combination, the suspension culture may be followed by adherent culture without any treatment, or mesodermal cells prepared by the suspension culture may be selected before the adherent culture. In the present description, "mesoderm" includes germ layers constituted by cells capable of producing, during development, the body cavity and mesothelium lining it, muscles, skeletons, dermis, connective tissues, heart/blood vessels (including vascular endothelium), blood (including blood cells), lymph vessels and spleen, kidney and ureter, and gonads (testis, uterus and gonadal epithelium). These can be detected by expression of markers such as T, KDR, FOXF1, FLK1 and/or BMP4. The cells preferably express KDR or FLK1.

In the present invention, the adherent culture may be carried out by co-culture with feeder cells. Examples of the feeder cells used in the co-culture include OP9 cells (Nishikawa, S. I. et al., Development 125, 1747-1757 (1998)) and END-2 cells (Mummery C, et al., Circulation. 107:2733-40 (2003)), but, in cases where the cultured cells are used as a material for cells to be transplanted, it is preferred, in view of prevention of contamination with other types of cells, that co-culture be not carried out.

In this process, the medium may be prepared using, as a basal medium, a medium for use in animal cell culture. Examples of the basal medium include IMDM medium, Medium 199, Eagle's Minimum Essential Medium (EMEM), α-MEM medium, Dulbecco's modified Eagle's Medium (DMEM), Ham's F12 medium, RPMI 1640 medium and Fischer's medium, and mixtures thereof. The medium is preferably RPMI 1640 medium. The medium may either contain serum or be serum-free. The culture medium may also contain, as required, one or more of serum replacements such as albumin, transferrin, Knockout Serum Replacement (KSR) (serum replacement for FBS in ES cell culture), fatty acid, insulin, collagen precursor, trace element, 2-mercaptoethanol, 3'-thiolglycerol and ITS supplement; and/or one or more of substances such as B27 supplement, N2 supplement, lipid, amino acid, L-glutamic acid, Glutamax (Invitrogen), non-essential amino acid, vitamin, cytokine, Wnt signaling inhibitor, antibiotic, antioxidant, pyruvic acid, buffer, inorganic salt and cyclosporin A. Examples of the cytokine include activin A and BMP4. Examples of the Wnt signaling inhibitor include XAV939 (Shih-Min A. Huang, et al., Nature 461, 614-620, 2009), vitamin A (retinoic acid), lithium, flavonoid, Dickkopf1 (Dkk1), insulin-like growth factor-binding protein (IGFBP) (WO2009/131166), and siRNAs against β-catenin.

Preferred examples of the medium include RPMI 1640 medium supplemented with B27 supplement, and, in cases where agents are further added, different agents may be added at different stages of culturing.

The culture temperature is not restricted and may be about 30 to 40° C., preferably about 37° C., and the culture is carried out under the atmosphere of $CO_2$-containing air, wherein the $CO_2$ concentration is preferably about 2 to 5%. The culture is carried out for a period required for cardiac troponin and/or αMHC to be expressed, and the culturing period is, for example, not less than 7 days.

In the present invention, examples of the method for producing cardiomyocytes and/or cardiac progenitor cells from pluripotent stem cells include a method wherein a Matrigel-coated culture dish is used and the cells are cultured first in RPMI 1640 medium supplemented with activin A and B27 supplement for 1 day, then in RPMI 1640 medium supplemented with BMP4, bFGF and B27 supplement for 4 days, and further in RPMI 1640 medium supplemented with Dkk1 and B27 supplement for 2 days.

The thus produced cardiomyocytes and/or cardiac progenitor cells may form a cell population only composed of cardiomyocytes and/or cardiac progenitor cells, but usually forms a cell population also containing other types of cells. In the latter case, it is necessary to extract cardiomyocytes and/or cardiac progenitor cells by the method of the present invention so as to increase the purity of the cardiomyocytes and/or cardiac progenitor cells.

<Method for Extraction or Detection of Cardiomyocytes and/or Cardiac Progenitor Cells>

For extraction or detection of cardiomyocytes and/or cardiac progenitor cells from a cell population containing the cardiomyocytes and/or cardiac progenitor cells, any of reagents having specific affinity to VCAM1, PDGFRβ or N-cadherin may be used, and, for example, an antibody, aptamer, peptide or compound that specifically recognizes such a protein may be used. The reagent is preferably an antibody or a fragment thereof.

In the present invention, the antibody may be either a polyclonal antibody or a monoclonal antibody. These antibodies may be prepared using a technique well known to those skilled in the art (Current protocols in Molecular Biology edit. Ausubel et al. (1987) Publish. John Wiley and Sons. Section 11.12-11.13). More particularly, in cases where the antibody is a polyclonal antibody, a protein encoded by VCAM1, PDGFRβ or N-cadherin which has been expressed in E. coli or the like and purified according to a conventional method, or a synthesized oligopeptide having a partial amino acid sequence of the protein, may be used to immunize a nonhuman animal such as a rabbit, followed by obtaining the antibody from the serum of the immunized animal according to a conventional method. On the other hand, the monoclonal antibody can be obtained from hybridoma cells prepared by cell fusion of spleen cells obtained from the above-described immunized nonhuman animal with myeloma cells (Current protocols in Molecular Biology edit. Ausubel et al. (1987) Publish. John Wiley and Sons. Section 11.4-11.11). Examples of the fragment of the antibody include parts (for example, Fab fragment) of the antibody and synthetic antibody fragments (for example, single-chain Fv fragment "ScFv"). Antibody fragments such as Fab and F(ab)$_2$ can also be prepared according to methods well known in the field of genetic engineering.

In order to distinguish and separate cells to which the reagent having affinity to VCAM1, PDGFRβ or N-cadherin is bound, the reagent may be bound or conjugated to a substance which can be detected, such as a fluorescent label, radioactive label, chemiluminescent label, enzyme, biotin or streptavidin, or to a substance which enables isolation and extraction of the cells, such as protein A, protein G, beads or magnetic beads.

The reagent having affinity to VCAM1, PDGFRβ or N-cadherin may also be indirectly labeled. The labeling can be carried out by various methods known to those skilled in the art, and examples thereof include a method wherein a preliminarily labeled antibody (secondary antibody) that specifically binds to an antibody against VCAM1, PDGFRβ or N-cadherin is used.

Examples of the method for detecting cardiomyocytes and/or cardiac progenitor cells include a method wherein the cells are isolated and purified by flow cytometry, followed by separately using a method for detection of the cells (for example, with a protein chip).

Examples of the method for extracting cardiomyocytes and/or cardiac progenitor cells include a method wherein large particles are conjugated to the reagent having affinity to VCAM1, PDGFRβ or N-cadherin to cause precipitation of the cells, a method wherein cells are selected using magnetic beads by the magnetism (e.g., MACS), a method wherein a fluorescent label is used to employ a cell sorter, and a method wherein a carrier (e.g., cell-concentrating column) to which an antibody or the like is immobilized is used.

In the present invention, when for example, more than 50%, 60%, 70%, 80% or 90% or 100% of a cell population comprising cardiomyocytes and/or cardiac progenitor cells obtained from pluripotent stem cells are identified as VCAM1 or N-cadherin positive cells or PDGFRβ negative cells, the step of detecting may be regarded as the step of extracting.

EXAMPLES

The present invention will now be described more concretely by way of Examples below, but, needless to say, the present invention is not restricted thereto.

Culture of Pluripotent Stem Cells

Human ES cells (KhES-1 and KhES-3) were received from Institute for Frontier Medical Sciences, Kyoto University (Suemori H, et al. Biochem Biophys Res Commun. 345:926-32, 2006). Human iPS cells (201B6, 201B7, 253G1, 253G4, TIG107-3F1, TIG107-4F1, TIG114-4F1 and TIG120-4F1) were received from Prof. Yamanaka at Kyoto University (Takahashi K, et al. Cell. 131:861-72, 2007; Nakagawa M, et al. Nat Biotechnol. 26:101-6, 2008). The human ES cells and human iPS cells were cultured on dishes coated with growth factor-reduced Matrigel (#354230; Becton-Dickinson), using a conditioned medium for MEFs (Mouse Embryo Fibroblasts) (culture supernatant prepared by culturing MMC (mitomycin C)-treated MEFs for 1 day in DMEM supplemented with 20% KSR, 4 ng/mL bFGF, 1 mM L-glutamine, 0.1 mM β-mercaptoethanol and 1% nonessential amino acids).

Example 1

Method for Inducing Cardiomyocytes/Cardiac Progenitor Cells

Human ES cells or iPS cells were plated at a density of 20 to 35×10$^4$ cells/200 mm$^2$ on a dish coated with Matrigel, and cultured in a conditioned medium for MEFs (culture supernatant prepared by culturing MMC-treated MEFs for 1 day in DMEM supplemented with 20% KSR, 4 ng/mL bFGF, 1 mM L-glutamine, 0.1 mM β-mercaptoethanol and 1% nonessential amino acids) for 2 days. Subsequently, the medium was replaced with RPMI1640 (Invitrogen) containing B27 supplement (without insulin) (Invitrogen) and 2 mM L-glutamine (RPMI/B27), which was supplemented with 100 ng/ml activin A (R & D Systems). On the next day, the medium was replaced with RPMI/B27 supplemented with 10 ng/ml BMP4 (R & D Systems), and the cells were cultured for 4 days. Thereafter, the medium was replaced with RPMI/B27 with no supplement. The culture was continued with replacement of RPMI/B27 every other day, and, from 4 days after the first replacement with RPMI/B27 with no supplement, pulsating cells were observed.

Evaluation of Cells with Cardiomyocyte/Cardiac Progenitor Cell Marker

Figure 1:
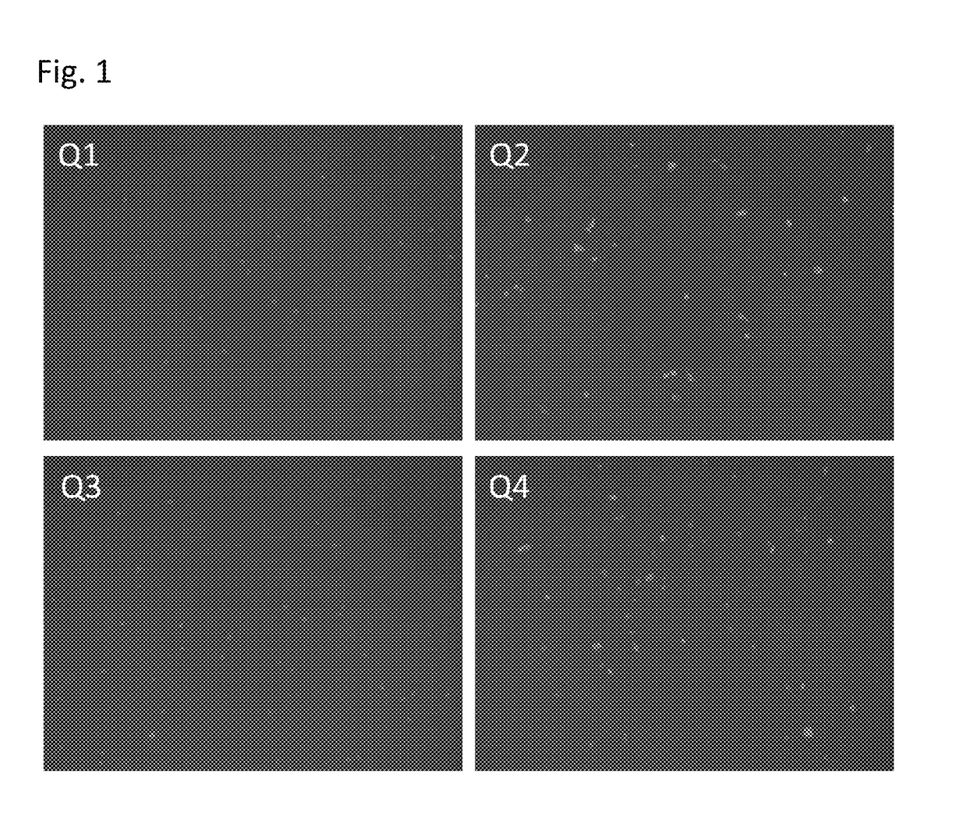
FIG. 1 shows immunostaining images (photograph) of cardiomyocytes derived from human iPS cells, which cardiomyocytes were prepared by sorting according to the categories of: VCAM1-negative and N-cadherin-positive (Q1); VCAM1-positive and N-cadherin-positive (Q2); VCAM1- negative and N-cadherin-negative (Q3); and VCAM1-positive and N-cadherin-negative (Q4); followed by 3 days of adherent culture. The immunostaining was performed with DAPI (blue) and cTnT (red).

Human iPS cell-derived cardiomyocytes/cardiac progenitor cells induced by the above-described method were divided into 4 categories, (1) VCAM 1-negative N-cadherin-positive, (2) VCAM1-positive N-cadherin-positive, (3) VCAM1-negative N-cadherin-negative and (4) VCAM1-positive N-cadherin-negative, and sorted. The cells were then plated on dishes coated with 0.1% gelatin and cultured in αMEM supplemented with 10% FBS (Invitrogen) for 3 days, and, as a result, it was confirmed that the VCAM1-positive N-Cadherin-positive cells contained the highest number of cTnT-positive cells, followed by the VCAM1-positive N-Cadherin-negative cells (FIG. 1).

Thus, it was suggested that, by using only VCAM1, or VCAM1 and N-cadherin as an index/indices, cardiomyocytes and cardiac progenitor cells can be identified.

Example 2

Method for Inducing Cardiomyocytes/Cardiac Progenitor Cell

Figure 2:
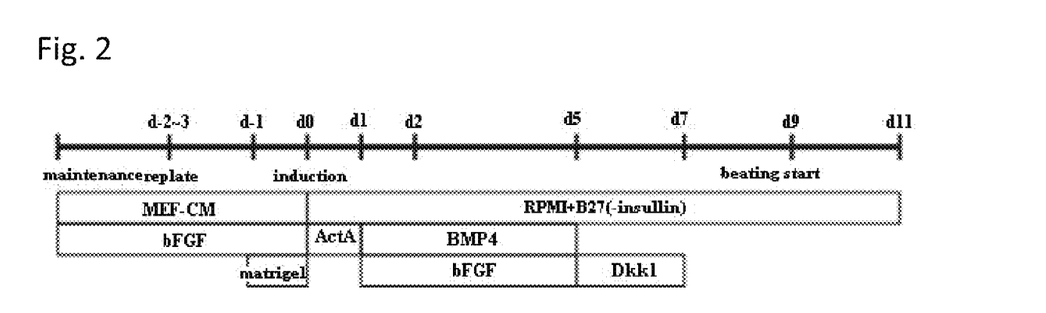
FIG. 2 shows a protocol for induction of differentiation of cardiomyocytes from pluripotent cells.

Human ES cells or iPS cells were plated at a density of 20 to $35 \times 10^4$ cells/200 mm² on a dish coated with Matrigel, and cultured in a conditioned medium for MEFs (culture supernatant prepared by culturing MMC-treated MEFs for 1 day in knockout DMEM supplemented with 20% KSR, 4 ng/mL bFGF, 1 mM L-glutamine, 0.1 mM β-mercaptoethanol and 1% nonessential amino acids) to which bFGF was added again at 4 ng/mL. This was followed by adding Matrigel to the medium and continuing the culture for 1 day. Subsequently, the medium was replaced with RPMI1640 (Invitrogen) containing B27 supplement (Invitrogen) and 2 mM L-glutamine (RPMI/B27), which was supplemented with 100 ng/ml activin A (R & D Systems). On the next day, the medium was replaced with RPMI/B27 supplemented with 10 ng/ml BMP4 (R & D Systems) and 10 ng/ml bFGF, and the cells were cultured for 4 days. Thereafter, the medium was replaced with RPMI/B27 supplemented with 10 ng/ml Dkk1. The medium was then replaced with RPMI/B27 medium, and the culture was continued for 4 days with replacement of the medium every other day. This protocol is shown in FIG. 2. One or two days after the first replacement with RPMI/B27 with no supplement, pulsating cells were observed.

Evaluation of Cells with Cardiomyocyte/Cardiac Progenitor Cell Marker

Figure 3:
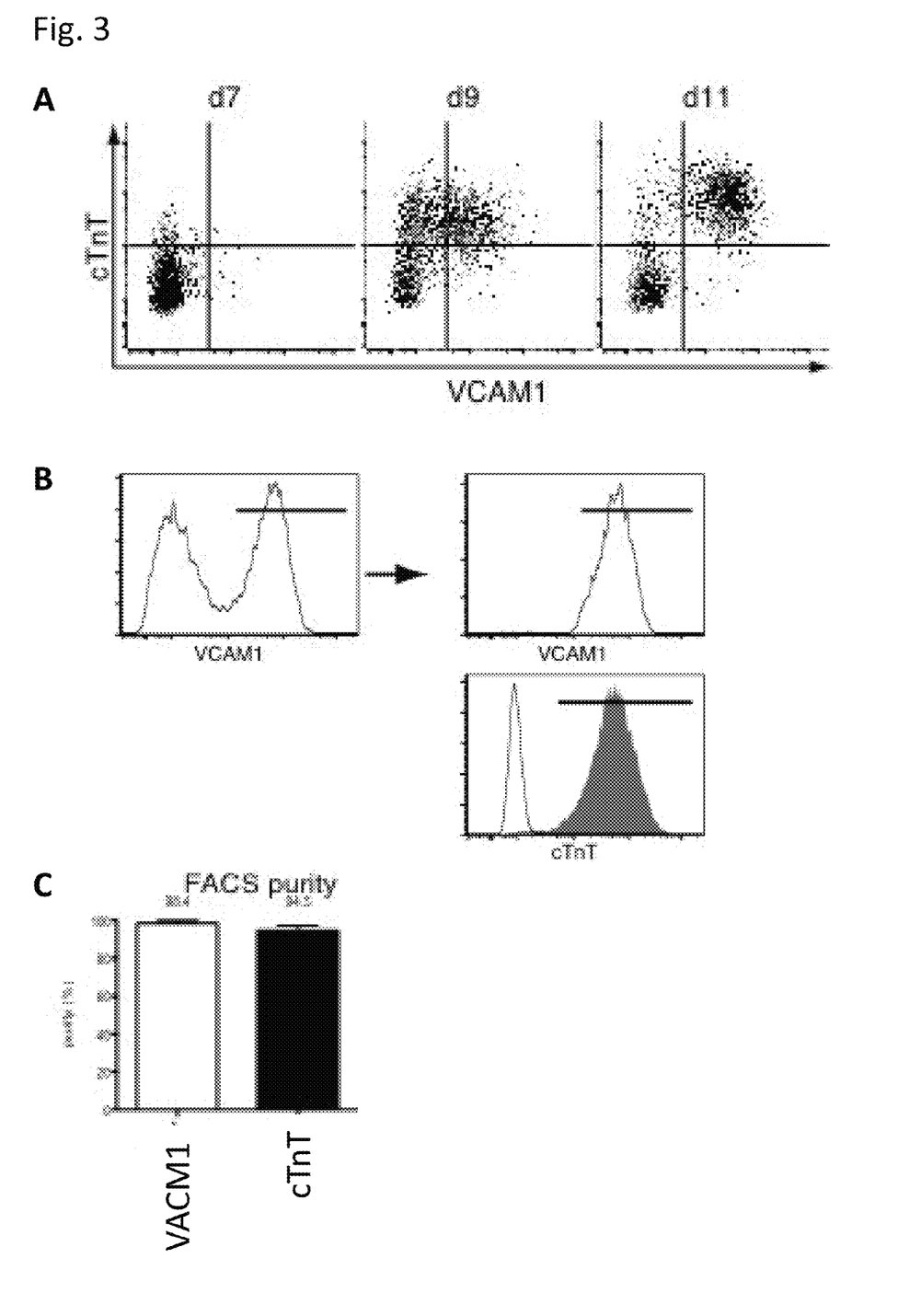
FIG. 3A shows results of flow cytometry on Day 7, 9 and 11 from the beginning of differentiation induction of pluripotent stem cells. In the diagram, the abscissa indicates the intensity of VCAM1 and the ordinate indicates the intensity of cTnT.
FIG. 3B shows results of flow cytometry on Day 11 from the beginning of differentiation induction of pluripotent stem cells. In the diagram, the abscissa indicates the intensity of VCAM1 (shown in the upper part) or cTnT (shown in the lower part), the ordinate indicates the cell number, and the area above each horizontal line indicates the region positive for VCAM1 or cTnT. In the lower diagram, the left peak indicates the result of isotype antibody staining (negative control), and the right gray peak indicates the result of cTnT antibody staining.
FIG. 3C shows the result of purification with MACS, wherein the positive rate of VCAM1 and the positive rate of cTnT are shown.

Human iPS cell (201B6)-derived cardiomyocytes/cardiac progenitor cells induced by the above-described method were stained with a VCAM1 antibody (BioLegend) and cTnT antibody (NeoMarker) on Days 7, 9 and 11 after the induction, and evaluated by flow cytometry. As a result, a correlation was found between the positivity of VCAM1 and the positivity of cTnT on Day 11 after the induction (FIG. 3A). Further, when the VCAM1-positive cells on Day 11 after the induction were purified, about 95% of the obtained cells were confirmed to be positive for cTnT (FIGS. 3B and C).

Figure 4:
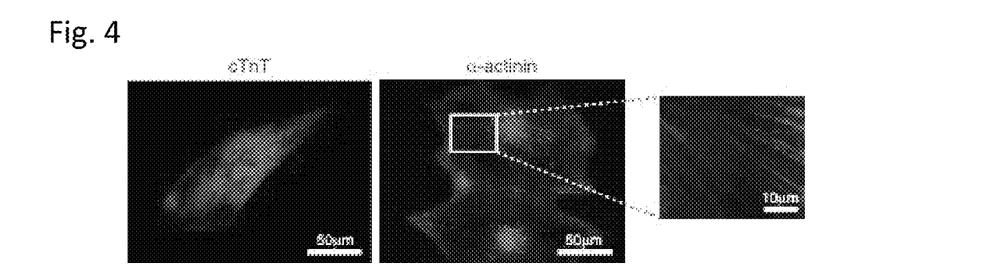
FIG. 4 shows immunostaining images(photograph) of VCAM1-positive cells cultured for 7 days after isolation of the cells, for cTnT (left panel) and α-actinin (right panel).
Figure 5:
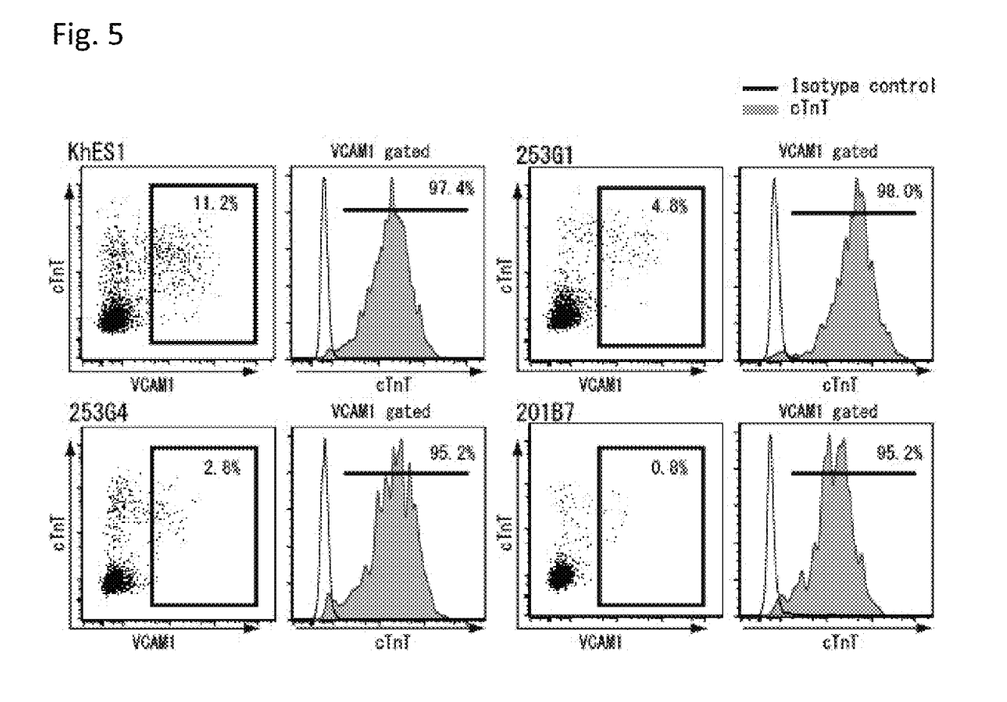
FIG. 5 shows the results of flow cytometry of cells whose differentiation was induced from an ES cell line (KhES1) and iPS cell lines (253G1, 253G4 and 201B7). The scatter plot (left panel) shows the fluorescence intensities for a cTnT antibody (ordinate) and a VCAM1 antibody (abscissa). The histogram (right panel) shows the intensity for the cTnT antibody in VCAM1-positive cells, and the number in the diagram indicates the content of the cells (cTnT-positive cells) within the range indicated by a horizontal line.

Further, when the cells purified on Day 11 after the induction were cultured for additional 7 days, actin filaments were observed together with cTnT (FIG. 4). It was further found that, also with a human ES cell line (KhES1) and other iPS cell lines (201B7, 253G1 and 253G4), cardiomyocytes and cardiac progenitor cells can be efficiently isolated by using the positivity of VCAM1 (FIG. 5). Thus, it was confirmed that cardiomyocytes and cardiac progenitor cells can be efficiently isolated/purified using the positivity of VCAM1 as an index.

Figure 6:
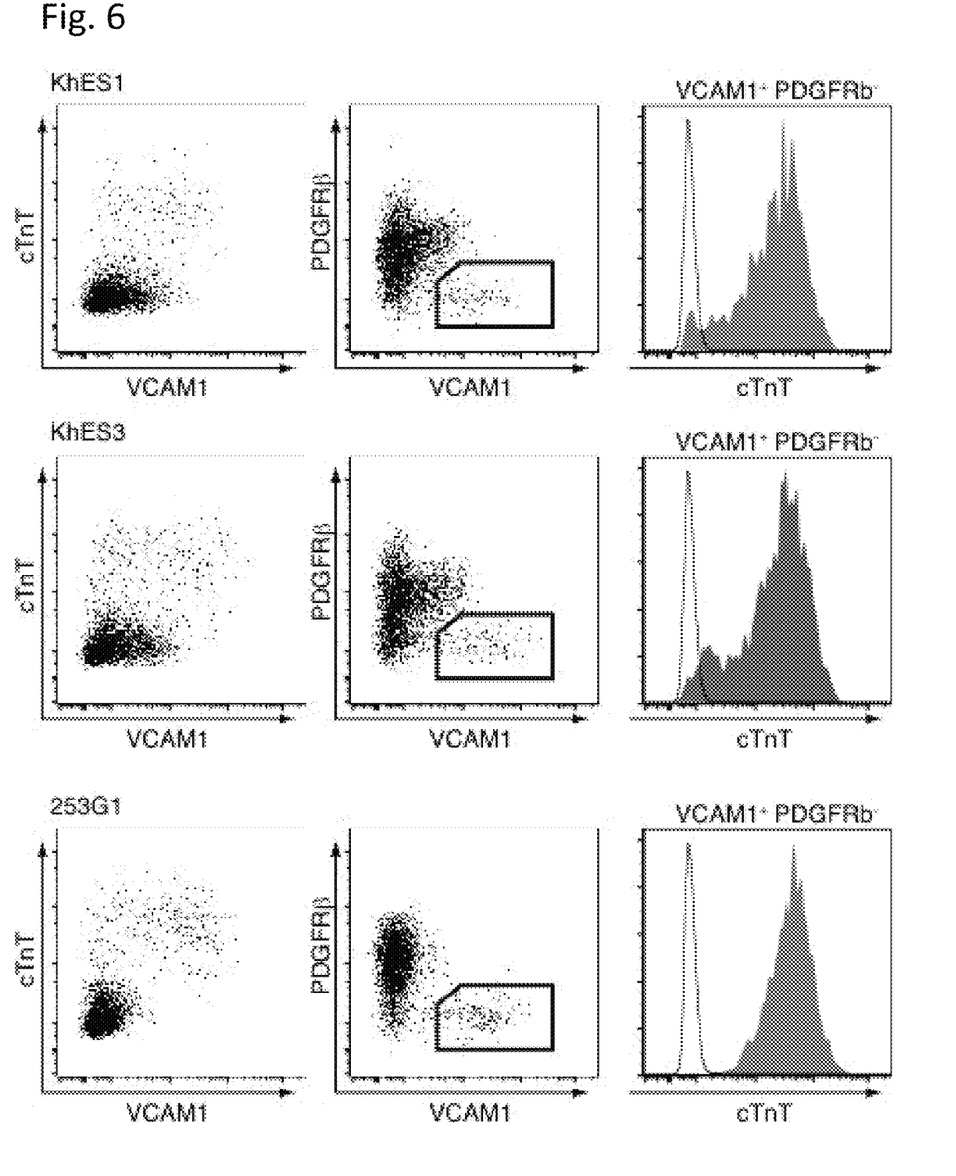
FIG. 6 shows the results of flow cytometry of cells whose differentiation was induced from various pluripotent stem cells (Kh-ES1 (top), Kh-ES3 (middle) and 253G1 (bottom)). In the left panel, the intensity of VCAM1 is taken along the abscissa, and the intensity of cTnT is taken along the ordinate. In the middle panel, the intensity of VCAM1 is taken along the abscissa, and the intensity of PDGFRβ is taken along the ordinate. The right panel shows the expression intensity of cTnT in VCAM1-positive PDGFRβ-negative cells (gray region).

Further, the cardiomyocytes and cardiac progenitor cells that were induced by the above-described method and derived from the human ES cells (KhES1 and KhES3) and iPS cells (253G1) were stained for VCAM1, cTnT and PDGFRβ and then analyzed with FACS. As a result, it was found that, in any of the cell lines, the VCAM1-positive PDGFRβ-negative cell population was composed of mostly cTnT-positive cells (FIG. 6). Thus, it was suggested that, by using the positivity of VCAM1 together with the negativity of PDGFRβ as indices, cardiomyocytes and cardiac progenitor cells can be identified more efficiently.

INDUSTRIAL APPLICABILITY

The present invention is useful in regenerative medicine and the like.

The invention claimed is:

1. A method for isolating a cardiomyocyte(s), comprising selecting for cells which are positive for vascular cell adhesion molecule-1 (VCAM1) from a cell population and isolating the VCAM1 positive cells.

2. The method according to claim 1, further comprising selecting for cells that are negative for platelet-derived growth factor receptor β (PDGFRβ).

3. The method according to claim 1, further comprising electing for cells that are positive for N-cadherin and isolating the VCAM1 positive and N-cadherin positive cells.

4. The method according to claim 1, wherein said cardiomyocyte(s) is/are a human cardiomyocyte(s).

5. The method according to claim 1, wherein said cell population is a cell population comprising cardiomyocytes the differentiation of which has been induced from pluripotent stem cells, or a cell population composed of cells from an isolated tissue.

6. The method according to claim 5, wherein said differentiation induction into cardiomyocytes is differentiation induction by culturing in a medium containing a cytokine(s).

7. The method according to claim 6, wherein said cytokine(s) is/are at least one cytokine selected from the group consisting of activin A and bone morphogenic protein 4(BMP4).

8. A method for detecting a cardiomyocyte(s), comprising detecting cells which are positive for VCAM1 in a cell population comprising cardiomyocytes.

9. The method according to claim 8, further comprising detecting cells which are negative for PDGFRβ.

10. The method according to claim 8, further comprising detecting cells which are positive for N-cadherin.

11. The method according to claim 8, wherein said cardiomyocyte(s) is/are a human cardiomyocyte(s).

12. The method according to claim 8, wherein said cell population is a cell population comprising cardiomyocytes the differentiation of which has been induced from pluripotent stem cells, or a cell population composed of cells from an isolated tissue(s).

* * * * *